United States Patent [19]

Wooley

[11] Patent Number: 4,710,511

[45] Date of Patent: Dec. 1, 1987

[54] ETODOLAC FOR INHIBITION OF JOINT ANKYLOSIS

[75] Inventor: Paul H. Wooley, Belle Mead, N.J.

[73] Assignee: American Home Products Corporation (Del.), New York, N.Y.

[21] Appl. No.: 923,373

[22] Filed: Oct. 27, 1986

[51] Int. Cl.$^4$ .............................................. A61U 31/40
[52] U.S. Cl. .................................................... 514/411
[58] Field of Search ........................................ 514/411

[56] References Cited

U.S. PATENT DOCUMENTS 4,533,551  8/1985  Martel ................................. 514/411

Primary Examiner—Stanley J. Friedman

[57] ABSTRACT

A method is disclosed for inhibiting joint ankylosis for the treatment of arthritides by administering an effective amount of etodolac.

3 Claims, No Drawings

ETODOLAC FOR INHIBITION OF JOINT ANKYLOSIS

BACKGROUND OF THE INVENTION (a) Field of the Invention

This invention relates to a novel therapeutic use of 1,8-diethyl-1,3,4,9-tetrahydropyrano[3,4-b]indole-1-acetic acid whose generic name is etodolac. More specifically this invention relates to a method of inhibiting joint ankylosis in mammals for the treatment of arthritides.

(b) Prior Art

The active agent of this invention, 1,8-diethyl-1,3,4,9-tetrahydropyrano[3,4-b]indole-1-acetic acid or a therapeutically acceptable salt thereof, is disclosed in U.S. Pat. No. 3,939,178. This active agent, hereinafter designated by its generic name etodolac, has been reported to have analgesic and anti-inflammatory properties. It has been further reported to be active in the treatment of adjuvant arthritis, a model of inflammatory arthritis sensitive to treatment with nonsteroidal anti-inflammatory drugs, in U.S. Pat. No. 4,533,551. Collagen-induced arthritis in mice is an experimental model of arthritis that lacks sensitivity to treatment with typical non-steroidal anti-inflammator drugs [Phadke K. et al.: "Evaluation of the effects of various antiarthritic drugs on type II collagen-induced mouse arthritis model", Immunopharmacology 10, 51–60 (1985)]. Collagen-induced arthritis is an experimental disease model with a number of pathological, histological, immunological, and genetic characteristics in common with rheumatoid arthritis (Trentham DE: "Collagen arthritis as a relevant model for rheumatoid arthritis: evidence pro and con," Arthritis Rheum 1982; 25: 911–916.). Collagen-induced arthritis represents an autoimmune disease, since the immunization of mice with heterologous type II collagen gives rise to an arthritogenic reaction against autologous collagen (Holmdahl R. Jansson L. Gullberg D. Forsberg PO, Rubin K and Klareskog L: "Incidence of arthritis and autoreactivity of anti-collagen antibodies after immunization of DBA/1 mice with heterologous and autologous collagen II," Clin Exp. Immunol 1985; 62:639–646.)

It has now been found unexpectedly that etodolac, either in its free acid form or in its therapeutically acceptable salt form, is useful for inhibiting joint ankylosis in mammals for the treatment of arthritides.

This finding, coupled with the fact that etodolac is a relatively safe drug, renders the method of this invention particularly useful and advantageous.

SUMMARY OF THE INVENTION

According to this invention a method is provided for inhibiting joint ankylosis for the treatment of arthritides in a mammal in need of said treatment, which comprises administering to the mammal an affective amount of etodolac, or a therapeutically acceptable salt thereof, and particularly for inhibiting joint ankylosis for the treatment of ankylosing spondylitis.

DETAILS OF THE INVENTION

According to the present method, etodolac, either in its free acid form or in the therapeutically acceptable salt form, is employed as the active agent. Examples of suitable salt forms are described in U.S. Pat. No. 3,939,178 and include the sodium, potassium, magnesium, triethylamine and benzylamine salt forms. A preferred salt form is the sodium salt, i.e. etodolac sodium.

Etodolac or a therapeutically acceptable addition salt thereof is administered to a mammal suffering from arthritides either orally or parenterally. For many reasons oral administration is preferred.

While etodolac or a therapeutivally acceptable salt thereof can be administered alone, e.g. as a sole compoennt of a filled capsule, it is preferred to formulate the compound in various dosage forms for oral or parenteral administration, e.g. tablets, or sterile solutions. Such formulations are described in U.S. Pat. No. 3,939,178, herein incorporated by reference in its entirety.

When utilizing etodolac or one of its above-noted salts as agents for inhibiting ankylosis, the total dose of active agent can range from about 50 milligrams to about 1000 milligrams per day with a preferred dosage range of from 200 to 600 milligrams per day. However, greater inhibition can be achieved with 1000 mg per day. Generally, a parenteral dose or an oral dose is administered in one to four applications per day, but more commonly twice a day. Such doses are considered to be an effective amount when, following their administration, or when the subjective symptoms complained of by said human beings are reported as having disappeared, or as being ameliorated or reduced in severity following such treatment.

The effectiveness of etodolac or its therapeutically acceptable salts as agents for inhibiting joint ankylosis in mammals for the treatment of arthritides is demonstrated by the effect of prolonged treatment with etodolac on the pathological and immonological characteristics of type II collagen-induced arthritis in animals as compared with vehicle treated animals in the following example.

A significant reduction in the maximum clinical score was observed, and this result was attributable to a reduction in number of joints progressing to ankylosis. At high doses (16 mg/kg/day), a significant delay in the onset of arthritis was also observed. This experimental arthritis model has been described in the literature as being insensitive to treatment with typical nonsteroidal anti-inflammatory drugs. No consistent variations were observed in the antibody response to type II collagen or in other immunological characteristics of the experimental arthritis.

EXAMPLE 1

Induction of collagen Arthritis

DBA/1 Lac J mice were purchased from Jackson Laboratories (Bar Harbor, Maine) and housed under specific pathogen-free conditions. Mice were randomly assigned to groups receiving etodolac at 3, 8, 12, or 16 mg/kg/day in 2% carboxymethylcellulose solution or vehicle alone. Dosing was commenced three days prior to immunization with collagen. Chick type II collagen was solubilized in 0.01M acetic acid at 2 mg/ml by overnight agitation at 4° C. and emulsified with an equal volume of Freund's Complete adjuvant. One hundred microliters of innoculum was injected intradermally at the base of the tail.

Assessment of arthritis

Mice were inspected daily for the onset of arthritis and assessed three times weekly for the progression of the disease. Constant tension caliper measurements were taken and recorded on an assessment sheet as an objective measure of paw thickness and ankle width in affected and unaffected limbs. A subjective clinical score was assigned to each limb, based on the following scale:

0 = normal limb appearance;
1 = erythema and edema;
2 = joint distortion, with or without erythema and edema;
3 = joint ankylosis, detected by manipulation.

The clinical score was judged by at least two observers, one kept unaware of the drug treatment of each animal. The clinical score was recorded on the individual assessment sheets. Also noted on the arthritis assessment sheet were the dates of disease onset and of peak inflammation index. The latter was calculated from the mean date of maximum joint swelling observed for each involved limb. At the end of 10 weeks of study, mice were sacrificed, and the peripheral limbs were removed at the hair line. Limbs were randomly assigned to be assessed histologically. Limbs for histological assessment were fixed in 10% formalin for a minimum of 24 hours and decalcified for 18 days in Surgipath (Fisher, New Brunswick). After alcohol and xylene processing, the joints were embedded in paraffin and orientated to cut lateral sections. Sequential 5 micron sections were cut to provide histological specimens for analysis from the tarsal and metatarsal joints of the rear paw and from the carpal and metacarpal joints of the front paw. The sections were stained with hematoxylin and eosin and coded for blind assessment of joint pathology. The following scoring system was used to assess sections:

0 = normal cartilage surfaces and synovial membrane (2-3 cells thick);
1 = synovial hypertrophy and cellular infiltrate;
2 = grade 1 plus pannus formation;
3 = grade 2 plus erosion of cartilage and subchondral bone;
4 = loss of joint integrity, massive erosion, bony ankylosis.

Immunological assessment

Sera samples were obtained from all mice prior to the commencement of any experimental procedure. Mice were also bled 14 and 28 days after immunization, at the onset of disease and after 10 weeks assessment. All sera samples were separated and stored at $-80°$ C., and all tests were performed concurrently after the conclusion of in vivo testing. Sera were assayed for antitype II collagen antibody using the micro-ELISA technique and for circulating IgG immunoglobulin using the radial immunodiffusion assay. Spleens were removed at the time of sacrifice, and the mitogen respones to Concanavalin A and Lipopolysaccharide determined.

Statistical analysis

Relevant information was derived from the arthritis assessment form and stored in the DBA/1 Lac J arthritis data base. This information included drug treatment, onset, number of involved joints, maximum clinical score, individual limb score, maximum swelling, inflammation peak, and the occurrence of remissions. The results of the serological and cell-mediated immunity assays were added. The data base was sorted by drug treatment within the individual experiments, and statistical analysis was performed on the data output for each of the factors using Students T test.

Pathological assessment

Forty mice were immunized with type II collagen. Twenty mice received 3 mg/kg/day of etodolac starting three days prior to immunization, and 20 mice received the vehicle control. No significant variations were observed between the groups with respect to arthritis incidence, onset of disease, or inflammation index. However, a significant decrease ($p<0.025$) in the maximum clinical score was seen in etodolac-treated animals. On further analysis, this was found to be due to a 50% decrease ($p<0.025$) in the number of joints progressing to ankylosis. A further forty mice were immunized with type II collagen. Ten mice received etodolac at 8 mg/kg/day; 10 mice received etodolac at 12 mg/kg/day; and 10 mice received etodolac at 16 mg/kg/day. Ten mice were treated with the vehicle control. The prevention of the disease progression to joint ankylosis was confirmed; no ankylosed joints were detected in mice receiving 8 mg/kg/day or 16 mg/kg/day ($p<0.025$), and only one mouse of the 12 mg/kg/day group progressed to joint ankylosis in the following Table I. In addition, mice receiving 16 mg/kg/day had a significant delay ($p<0.05$) in the onset of arthritis. These results indicate that etodolac had a retarding effect upon the progression of collagen induced arthritis. The histological score was compared to the observed clinical score for the same limbs in several experiments. A correlation was observed between the histological and pathological findings; namely, cellular infiltrate, synovial hypertrophy and pannus formation were frequently seen during clinical score 1, erosion of cartilage and bone during clinical score 2, and massive erosions and loss of joint integrity were confined to clinical score 3. Since this relationship was seen in both control- and etodolac-treated animals, it was concluded that the clinical scores accurately reflected a change in joint pathology.

TABLE I

| Treatment | Dose | Incidence % | Onset Day Mean S.E. | Involved Limbs Mean S.E. | Clinical Score Mean S.E. | Inflammation Index Mean S.E. | Ankylosis % | Remission % |
|---|---|---|---|---|---|---|---|---|
| Etodolac | 8 mg/kg | 100 | 32.60 (2.2) | 3.10 (0.4) | 6.20 (0.7) | 18.80 (2.7) | 0.00* | 5.00 |
| Etodolac | 12 mg/kg | 90 | 32.40 (1.7) | 3.30 (0.2) | 6.30 (0.7) | 14.40 (2.4) | 5.50 | 8.30 |
| Etodolac | 16 mg/kg | 80 | 44.00(3.1)+ | 2.30 (0.5) | 3.60 (0.8)* | 21.20 (2.2) | 0.00* | 6.30 |
| Control |  | 90 | 34.00 (3.2) | 3.20 (5.0) | 6.70 (0.9) | 15.00 (4.2) | 13.90 | 0.00 |

S.E. — Standard Error
+ - $p < 0.05$
*$p < 0.025$

Immunological assessment

The results of the cellular and serological immunology assays are shown in the following Table II. In mice receiving 3 mg/kg/day etodolac, higher anti-collagen antibody levels ($p<0.05$) were seen in comparison to vehicle treated mice at the onset of disease, but after 10 weeks the levels were similar. No significant variations were observed in IgG levels or mitogen responses. Higher anti-collagen antibody levels were also observed in the group of mice receiving 12 mg/kg/day both at the onset of disease (p<0.01) and after 10 weeks (p<0.05). Mice receiving 8 mg/kg/day and 16 mg/kg/day did not show any significant variations in anti-collagen antibody levels or mitogen responses but were observed to have a more rapid fall in circulating IgG levels (p<0.01) compared to control mice at the conclusion of the study.

TABLE II

|  |  | ANTI-COLLAGEN ANTIBODY | | | CON A RESPONSE | | LPS RESPONSE | |
|---|---|---|---|---|---|---|---|---|
| Treatment | Dose | Day 14 Mean S.E. | Day 28 Mean S.E. | Mean S.E. | Onset Mean S.E. | Bleedout Mean S.E. | S.I. Mean | S.I. S.E. |
| Etodolac | 3 mg/kg | 255 (60) | 379 (78) | 953 (281)+ | 164 (24) | 19.40 (6.5) | 8.32 | (0.8) |
| Control |  | 250 (80) | 290 (52) | 466 (58) | 226 (63) | 21.00 (7.5) | 8.48 | (0.8) |
| Etodolac | 8 mg/kg | 236 (24)* | 177 (15) | 233 (20) | 179 (28) | 1.76 (0.3) | 0.51 | (0.1) |
| Etodolac | 12 mg/kg | 552 (61) | 378 (64) | 383 (51)* | 330 (73)* | 1.75 (0.4) | 0.40 | (0.1) |
| Etodolac | 16 mg/kg | 503 (190) | 407 (82) | 325 (85) | 291 (61) | 1.39 (0.3) | 0.93 | (0.2) |
| Control |  | 465 (51) | 257 (38) | 189 (29) | 162 (22) | 1.72 (0.3) | 0.77 | (0.2) |
|  |  | IMMUNOGLOBULIN G LEVELS | | | | | | |
|  |  | Prebleed Mean S.E. | Day 14 Mean S.E. | Day 28 Mean S.E. | Onset Mean S.E. | Bleedout Mean S.E. | | |
| Etodolac | 3 mg/kg | 295 (13) | 2066 (223) | 2071 (118) | 2542 (170) | 1473 (79) | | |
| Control |  | 392 (45) | 2452 (232) | 1854 (175) | 2348 (136) | 1499 (22) | | |
| Etodolac | 8 mg/kg | 204 (14) | 955 (116) | 1181 (123)* | 1369 (224) | 1185 (129)* | | |
| Etodolac | 12 mg/kg | 237 (28) | 1448 (291) | 1499 (199) | 1557 (300) | 1387 (106) | | |
| Etodolac | 16 mg/kg | 190 (12) | 809 (99) | 1102 (174)* | 1270 (265) | 1099 (106)* | | |
| Control |  | 236 (42) | 999 (110) | 1882 (177) | 1659 (137) | 1793 (199) | | |

CON A Response = Mitogen response to Concanavalin A
LPS Response = Mitogen response to Lipopolysaccharide
S.E. = Standard Error
+ = P < 0.05
*p < 0.01

Of the three types of joint ankylosis associated with arthritides, i.e. diseases of the peripheral joints such as in osteoarthritis and rheumatoid arthritis, and disease of the vertebrae, such as in ankylosing spondylitis, these data indicate that the treatment with etodolac would be most effective in inhibiting disease progression in humans suffering from ankylosing spondylitis.

I claim:

1. A method for inhibiting joint ankylosis for the treatment of ankylosing spondylitis in a mammal in need of such treatment which comprises administering to the mammal an effective amount of etodolac or a therapeutically acceptable salt thereof.

2. The method of claim 1 in which the effective amount of etodolac is within the range of from about 50 mg to about 1000 mg per day.

3. The method of claim 1 in which the effective amount of etodolac is within the range of 600 mg to 1000 mg per day.

* * * * *